United States Patent [19]

Uemura et al.

[11] Patent Number: 4,526,782
[45] Date of Patent: Jul. 2, 1985

[54] PROCESS FOR RECOVERING INTERFERON

[75] Inventors: Yahiro Uemura, Hirakata; Hirofumi Arimura, Toyonaka; Hiroshi Morise, Hirakata; Satoshi Funakoshi, Katano; Tadakazu Suyama, Kyoto, all of Japan

[73] Assignee: The Green Cross Corporation, Osaka, Japan

[21] Appl. No.: 432,909
[22] PCT Filed: Feb. 17, 1981
[86] PCT No.: PCT/JP81/00030
    § 371 Date: Sep. 27, 1982
    § 102(e) Date: Sep. 27, 1982
[87] PCT Pub. No.: WO82/02834
    PCT Pub. Date: Sep. 2, 1982
[51] Int. Cl.$^3$ .............. A61K 45/02; C07G 7/00; C12P 21/00
[52] U.S. Cl. .................. 424/85; 260/112 R; 435/68
[58] Field of Search .............. 424/85; 435/68, 811; 260/112 R

[56] References Cited

FOREIGN PATENT DOCUMENTS 5102519  8/1980  Japan.

OTHER PUBLICATIONS

Chemical Abstracts, vol. 95, Abst. No. 12751v, 1981.
Chemical Abstracts, vol. 94, Abst. No. 180664s, 1981.
Chemical Abstracts, vol. 94, Abst. No. 180663r, 1981.

*Primary Examiner*—Blondel Hazel
*Attorney, Agent, or Firm*—Cushman, Darby & Cushman

[57] ABSTRACT

Interferon can be recovered simply by contacting an aqueous solution containing interferon which is induced and produced from cells of human origin capable of producing interferon, with a siliceous substance to adsorb interferon on it and eluting the adsorbed interferon with an aqueous solution containing a nonionic surfactant, preferably further containing an acriflavine such as acrinol.

9 Claims, No Drawings

PROCESS FOR RECOVERING INTERFERON

TECHNICAL FIELD

This invention relates to a process for recovering on an industrial scale an interferon produced by induced cells of human origin.

BACKGROUND ART

Interferon is a certain type of glycoprotein induced in human and other animal cells by viral or other stimuli. The interferon has an inhibitory action for the growth of virus, bacteria, or protozoa in cells. In order to apply it in man as a medicine, it is necessary to obtain the interferon produced in human cells because of its species specific. To obtain large quantities of human interferon, it is necessary to collect a large quantity of human lymphocytes, human fibroblasts, or human lymphoblasts, etc. then to stimulate them by suitable means to produce the interferon, and to recover the formed interferon in a high yield.

The conventional recovering methods, however, have such defects that they are too complicated in the procedure and are too time-consuming to be carried out on a commercial scale, and further they have an additional disadvantage of low material yield.

DISCLOSURE OF INVENTION

The present inventors have conducted researches for many years on the method of recovering interferon in a good yield by simple operations, and found that a silicic acid-containing material such as bentonite, acid clay, etc. adsorbs interferon specifically. They further continued studies on the elution of interferon from the adsorbent and found that interferon is specifically eluted from the adsorbent when an aqueous solution containing a nonionic surfactant or containing in addition acriflavines is applied. Based on the new knowledge, they have accomplished the present invention, that is, they were successful in recovering interferon in a good yield on an industrial scale by simple operations.

This invention provides a process for recovering interferon, which comprises contacting a silicic acid-containing material with an aqueous solution containing interferon induced and produced from cells of human origin, to adsorb the interferon on the composition and thereafter eluting the adsorbed interferon with an aqueous solution containing a nonionic surfactant or which may additionally contain an acriflavine.

BEST MODE FOR CARRYING OUT THE INVENTION

Any of known interferon-producing cells such as leukocytes; lymphocytes; reticuloendothelial cells such as those of the peritoneal cavity, lung, and spleen; cultured human lymphoblast-like cells, can be used as the cells of human origin in this invention. However, preferred in view of productivity are human leukocytes and cultured human lymphoblast-like cells from the productivity point of view, and among the latter cells the Namalwa strain is particularly preferred. The Namalwa strain is an established cell line selected from 20 established lymphocytes originated from Burkitt's lymphoma patients or leukemia patients, and is known at present as a cell most productive of interferon [Intern. J. Cancer, 11, No. 327 (1973) and J. Clinical Microbiol, 1, No. 1 (1975)].

The acid ($SiO_2$) containing material, usable in this invention includes bentonite, acid clay, kaolin, magnesium aluminosilicate, and compounds corresponding thereto. The concentration of the silic acid-containing composition used is within the range of 0.001–4.0 W/V%, usually 0.01–1.0 W/V%, based on the interferon-containing aqueous solution. The contact of the silicic acid-containing composition with the interferon-containing aqueous solution is usually effected batchwise by adding the former to the latter. The contact is preferably effected at a pH of 5–9 with stirring. The temperature and period of contact may be room temperature and 1–5 hours, respectively. By such a contacting operation interferon is adsorbed on the silicic acid-containing composition, and this adsorption is extremely specific.

The elution of the adsorbed interferon is effected with an aqueous solution containing a nonionic surfactant, preferably with an aqueous solution containing both a nonionic surfactant and an acriflavine, after the silicic acid-containing composition has been separated from the aqueous solution and washed. The pH of the eluent aqueous solution is preferably adjusted to 1.5–9.0, and the acriflavine concentration is usually 0.01–2.0 W/V%. (W/V% means percentage of the weight of a solute based on the volume of a solution; the same applies herein.) The use of acrinol as the acriflavine is advantageous in that it is easily soluble in water. As the nonionic surfactant to be used, polyoxyethylene group surfactants such as those of the sorbitan monoalkyl ester type, alkyl ether type, and of polyoxyethylene-polyoxypropylene copolymer type are advantageous in that they scarcely bind to protein. The surfactant concentration is 0.001–4.0 W/V%. These nonionic surfactants have a markedly elevated elution effect when used in combination with an acriflavine, though they have a certain degree of elution effect even when used singly.

When the starting interferon has been roughly purified, the eluted interferon, as it is or after addition of a stabilizer, is dialyzed for desalting, sterilized through bacterial filtration, subdivided into portions, and then lyophilized to obtain a dry preparation. When the starting interferon has not been purified the eluted interferon is roughly purified by desalting, dialysis, concentrating, etc., then highly purified by a known method, and is finished to a dry preparation.

Examples of purification methods which can be incorporated into the process of this invention are as follows: the ethanol fractionation method [Tissue Culture Association, In Proceedings of a Tissue Culture Association Work Shop In Vitro, Paper No. 3 (1973)], a purification method wherein column chromatography by use of a weak acid or weak base ion exchanger is combined with gel filtration (Japanese Patent Publication No. 34442/1976), a purification method using ammonium chloride or dextran [Ann. Med. Exp. Fenn. 44, 265–273 (1966) and ibid., 45, 20–29 (1967)], and a fractionation method using a strong acid cation exchanger (Japanese patent application Laid-open No. 89011/1979; Applicant: the Green Cross Corporation).

The interferon recovery process of this invention is the same as or higher in recovery yield than conventional processes, and its operative steps which comprise contacting an interferon-containing aqueous solution with a silicic acid-containing composition of matter and eluting the interferon with an aqueous solution containing a nonionic surfactant and an acriflavine, are both simple, that is, the operative steps have been simplified to a great degree. For these reasons, the process of this invention is exceedingly attractive as an industrial scale process for recovering interferon.

This invention will be futher illustrated by way of comparative experiments and of preferred embodiments; however, the invention is not limited to these examples.

The activity of interferon in these examples was determined by the method of 50% plague reduction using Vesicular stomatitis virus and the FL cells originated from human amnion. The titer of interferon of each specimen was expressed in International units (IU) calculated from the assay of the sample and the standard sample of interferon. [Saishin-igaku (Modern Medicine), 29, No. 4, 660 (1974)].

COMPARATIVE EXPERIMENTS

Experiments were made on adsorbents and eluents for interferon, each using about 5 l of an aqueous solution of crude interferon (specific activity 3000 i u/mg of protein) obtained from a culture system for lymphocytes of human vein origin. The adsorbents and the compositions of the eluents used are as shown in Table 1. In the experimens, the aqueous solution of crude interferon was centrifuged, the supernatant was collected, each of the different adsorbents was added thereto in a proportion of 1 W/V%, the mixture was stirred at room temperature for 2 hours, and then the adsorbent was recovered by centrifugation. After washing, the adsorbent was treated with each of the different eluents to elute the interferon. The interferon-containing eluate was dialyzed, concentrated, and then the activity of the resulting solution was measured to calcualted the recovery yield. From the results, as shown in Table 1, the eluents containing both a nonionic surfactant and an acriflavine were found to have a significant eluting effect.

TABLE 1

Recovery yields with different eluents and adsorbents

| Eluent | | | Recovery yield | | |
|---|---|---|---|---|---|
| Base solution | Additive (A) | Additive (B) | Bentonite | Acid clay | Magnesium aluminosilicate |
| HCl aq. of pH 2 | — | — | 0 | 0 | 0 |
| HCl aq. of pH 2 | 1.0 M NaCl | — | 0 | 0 | 0 |
| 4% Citric acid aq. of pH 2.3 | — | — | 0 | 0 | 0 |
| Phosphate aq. of pH 8 | — | — | 0 | 0 | 0 |
| Phosphate aq. of pH 8 | 1.0 M NaCl | — | 0 | 0 | 0 |
| Barbital aq. of pH 10 | — | — | 0 | 0 | 0 |
| HCl aq. of pH 2 | Polyoxyethylene-polyoxy propylene copolymer (Mol. Wt 16,500) 3 W/V % | — | 35 | 35 | 37 |
| HCl aq. of pH 2 | Polyoxyethylene polyoxy propylene copolymer (Mol. Wt 16,500) 0.001 W/V % | Acrinol 1 W/V % | 50 | 50 | 53 |
| HCl aq. of pH 2 | Polyoxythylene polyoxy propylene copolymer (Mol. Wt 16,500) 2 W/V % | Acrinol 0.5 W/V % | 50 | 52 | 55 |
| HCl aq. of pH 2 | Polyethylene polyoxy propylene copolymer (Mol. Wt 16,500) 2 W/V % | Acrinol 0.01 W/V % | 45 | 48 | 48 |
| HCl aq. of pH 2 | — | Acrinol 2 W/V % | 40 | 38 | 39 |
| HCl aq. of pH 2 | Polyoxyethylene-sorbitan monooleate 2 W/V % | Acrinol 0.5 W/V % | 51 | 52 | 53 |
| HCl aq. of pH 2 | Polyoxyethylene-(40)-stearate 2 W/V % | Acrinol 0.5 W/V % | 50 | 51 | 52 |
| HCl aq. of pH 2 | Hardened caster oil-polyoxyethylene-(40)-ether 2 W/V % | Acrinol 0.5 W/V % | 50 | 52 | 52 |

EXAMPLE 1

Lymphocytes of human vein origin were cultivated in a MEM medium containing 5% of human albumin, and interferon was induced by Sendai virus, and then the pH was adjusted to 2 with hydrochloric acid to inactivate the Sendai virus used as an inducer. The resulting raw interferon liquor was centrifuged to collect the supernatant. The pH of the collected supernatant was returned to neutrality, 1.0 W/V% of bentonite was added thereto, and the mixture was stirred for 2 hours to adsorb interferon on the bentonite. The bentonite was collected by centrifugation, an aqueous solution containing 1 W/V% of NaCl was added thereto in an amount of twice the wet weight of bentonite, and after thorough stirring, the bentonite was collected again by centrifugation. After two repetitions of this operation, an aqueous solution containing 0.5% of acrinol and 2% of a polyoxyethylene-polyoxypropylene copolymer (trade name: Pluronic F 68; supplied by Wyandotte Chem. Corp.) was added to the bentonite collected, and the mixture was adjusted to pH 2.0 with I N hydrochloric acid and stirred at 37° C. for 1 hour to elute the interferon. The eluate was then dialyzed, using 0.05 M tris-hydrochloric acid buffer at 4° C. for about 12 hours, to concentrate and obtain purified interferon. The recovery yield was 50% based on the crude interferon activity in the starting culture calculated as 100%, and the degree of purification was 1000 times.

The concentrated solution of purified interferon was sterilized by bacterial filtration, subdivided into portions, and lyophilized to a dry preparation. The preparation was administered to mice and rabbits in a dose of $1 \times 10^6$ IU/kg, and observed for 7 days. As a result, no abnormality such as an increase or decrease in body weight and pilocrection was detected.

EXAMPLE 2

Purified interferon was obtained in the same manner as in Example 1, except that kaolin was added to a concentration of 1.0 W/V% in place of bentonite. The recovery yield was 56% and the degree of purification 950 times. The same tests of the resulting dry preparation on mice and rabbits as those in Example 1 showed no abnormality.

EXAMPLE 3

Interferon was produced by proliferating established human lymphocytes (Namalwa cells) using a liquid culture RPMI 1640 (Nissui Pharmaceutical Co.) and adding Sendai virus thereto as an inducer. The interferon was treated in the same manner as in Example 1 to obtain purified interferon. The recovery yield was 53% and the degree of purification 980 times. The same tests of the obtained dry preparation on mice and rabbits as those in Example 1 showed no abnormality.

We claim:

1. A process for recovering interferon comprising the steps of (1) contacting an aqueous solution containing interferon, which is induced and produced from cells of human origin, with a silicic acid containing adsorbent selected from the group consisting of bentonite, acid clay, kaolin and magnesium silicate thereby absorbing the interferon on the adsorbent, and (2) eluting the adsorbed interferon with a polyoxyethylene group surfactant-containing aqueous solution.

2. A process according to claim 1, wherein said aqueous solution containing interferon is of human leukocyte origin.

3. A process according to claim 1, wherein said aqueous solution containing intereferon is of cultured human lymphoblast-like cell origin of the Namalwa strain.

4. A process according to claim 1, wherein said polyoxyethylene group surfactant-containing aqueous solution further contains acrinol.

5. A process according to claim 1, wherein said polyoxyethylene group surfactant is selected from the group consisting of a sorbitan monoalkyl ester type, an alkyl ether type and a polyoxyethylene-polyoxypropylene copolymer type.

6. A process according to claim 1, wherein the adsorption is carried out at a pH of 5-9.

7. A process according to claim 1, wherein the elution is effected at a pH of 1.5-9.0.

8. A process according to claim 1, wherein the concentration of polyoxyethylene group surfactant in the eluent is 0.001-4.0 W/V %.

9. A process according to claim 4, wherein the concentration of an acrinol in the eluent is 0.01-2.0 W/V %.

* * * * *